United States Patent
Jelatis et al.

(10) Patent No.: US 8,347,365 B2
(45) Date of Patent: Jan. 1, 2013

(54) SYSTEM AND METHOD FOR CONFIRMING IDENTITY AND AUTHORITY BY A PATIENT MEDICAL DEVICE

(75) Inventors: George D. Jelatis, Minneapolis, MN (US); Scott J. Healy, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1131 days.

(21) Appl. No.: 12/057,272

(22) Filed: Mar. 27, 2008

(65) Prior Publication Data

US 2008/0244717 A1   Oct. 2, 2008

Related U.S. Application Data

(60) Provisional application No. 60/908,958, filed on Mar. 29, 2007.

(51) Int. Cl.
*G06F 7/04* (2006.01)
(52) U.S. Cl. ............................................. 726/5; 713/176
(58) Field of Classification Search .................. 713/156, 713/168, 176, 177; 726/2–5; 607/31, 32
See application file for complete search history.

(56) References Cited

U.S. PATENT DOCUMENTS

| | | | |
|---|---|---|---|
| 6,024,699 A | 2/2000 | Surwit et al. | |
| 6,083,248 A | 7/2000 | Thompson | |
| 6,168,563 B1 | 1/2001 | Brown | |
| 6,171,256 B1 | 1/2001 | Joo et al. | |
| 6,416,471 B1 | 7/2002 | Kumar et al. | |
| 6,827,670 B1 | 12/2004 | Stark et al. | |
| 7,027,872 B2 | 4/2006 | Thompson | |
| 7,155,290 B2 | 12/2006 | Von Arx et al. | |
| 2006/0156416 A1* | 7/2006 | Huotari et al. | 726/27 |
| 2008/0082830 A1* | 4/2008 | Goulet | 713/177 |

OTHER PUBLICATIONS

Schneier et al., "Applied Cryptography, Second Edition," Applied Cryptogrpahy, Protocols, Algorithms, and Source Code in C, John Wiley & Sons, Jan. 1, 1996, XP002306621, ISBN: 978-0-471-11709-4, pp. 574-576, New York, US.

Chadwick et al., "Role-Based Access Control With X.509 Attribute Certificates," IEEE Internet Computing, IEEE Service Center, vol. 7, No. 2, Mar. 1, 2003, XP002384681, ISSN: 1089-7801, pp. 62-69, New York, US.

(Continued)

*Primary Examiner* — Edward Zee
*Assistant Examiner* — Suman Debnath
(74) *Attorney, Agent, or Firm* — Pauly, DeVries Smith & Deffner, L.L.C.

(57) ABSTRACT

A system and method for confirming identity and authority by a patient medical device is provided. Master credentials are issued to a requesting device and a receiving device from an authorizing agent. The master credentials include the authorizing agent's public key and a digital signature of a root certification authority. Device credentials are issued to the requesting device from the authorizing agent. The device credentials include the requesting device's public key and the authorizing agent's digital, signature. Identification credentials are provided to the receiving device and include the device credentials and the requesting device's digital signature. The requesting device is authenticated. The authorizing agent's digital signature in the device credentials is checked using the authorizing agent's public key in the master credentials of the receiving device. The requesting device's digital signature in the identification credentials is checked using the requesting device's public key in the device credentials.

20 Claims, 5 Drawing Sheets

OTHER PUBLICATIONS

"Information Technology—Open Systems Interconnection—The Directory: Public-Key and Attribute Certificate Frameworks; X.509 (Aug. 2005)" ITU-T Standard in Force (I), International Telecommunication Union, No. X.509 (Aug. 2005), Aug. 29, 2005, XP017405086, Geneva, CH.

Neuman—Institute of Electrical and Electronics Engineers: "Proxy-Based Authorization and Accounting for Distributed Systems," Proceedings of the International Conference on Distributed Computing Systems, May 1993, Proc. of the International Conference on Distributed Computing Systems, Los Alamitos, IEEE Comp. Soc. Press, US, vol. Conf. 13, May 25, 1993, XP000399398, ISBN: 978-0-8186-3770-4, pp. 283-291, Pittsburgh.

Health Insurance Portability and Accountability Act of 1996, Pub. L. No. 104-191, 110 Stat. 1936 (1996).

E. Hammond, "National Committee on Vital and Health Statistics, Subcommittee on Health Data Needs, Standards and Security," http://www.ncvhs.hhs.gov/970211t3.htm, pp. 1-4 (Feb. 11, 1997).

Security and Electronics Signature Standards, 63 Fed. Reg. 155 (proposed Aug. 12, 1998).

W. Diffie, "The First Ten Years of Public-Key Cryptography," Proceedings of the IEEE, vol. 76, No. 5, pp. 560-577 (May 1988).

PCT Notification Concerning Transmittal of International Preliminary Report on Patentability, from International Application No. PCT/US2008/058772, corresponding to U.S. Appl. No. 12/057,272,, mailed Oct. 8, 2009, 9 pages.

PCT International Search Report and Written Opinion, from International Application No. PCT/US2008/058772, corresponding to U.S. Appl. No. 12/057,272, mailed Sep. 1, 2008, 4 pages.

\* cited by examiner

SYSTEM AND METHOD FOR CONFIRMING IDENTITY AND AUTHORITY BY A PATIENT MEDICAL DEVICE

CROSS-REFERENCE TO RELATED APPLICATION

This non-provisional patent application claims priority under 35 U.S.C. §119(e) to U.S. Provisional Patent application Ser. No. 60/908,958, filed Mar. 29, 2007, the disclosure of which is incorporated by reference.

FIELD

The invention relates in general to medical device interrogation and, specifically, to a system and method for confirming identity and authority by a patient medical device.

BACKGROUND

Patient medical devices and monitors (collectively "PMDs"), particularly implantable PMDs, generally require periodic interrogation by programmers or personal communicators (collectively PMD interrogation devices, or "PIDs") to retrieve recorded patient physiometry and parametric data and to perform device programming. Conventionally, interrogation and programming have been limited to in-clinic or hospital settings using inductive or near proximity telemetry. The visual and physical closeness of the patient, caregiver, and PID provide assured identification and authorization. "Identification" refers to knowing the positive identity of the person that is performing the procedure. "Authorization" refers to the patient granting permission to that person to perform with the procedure. Physical identification and authorization minimized, the chances of interrogation or programming being misdirected to the wrong PMD or being performed without permission or covertly, for instance, through a stolen or altered programmer, PMDs have become increasingly capable and autonomous as onboard processing, data storage, and battery efficiency have improved. PMDs can now use radio frequency (RF) telemetric or similar long range interrogation interfaces. As the range of RF interrogation interfaces can be up to several meters, visual and physical identification can be ineffective. RF interrogation thus opens the possibility of unauthorized programmers being used for interrogation or programming, either without permission through a stolen, modified, or non-manufacturer programmer, or by innocent mistake, such as where a physician interrogates the wrong device, such as a PMD located in an adjacent room.

Consequently, to ensure patient safety, the identity of a PID and the authority of that PID to interrogate or program a PMD should be confirmed whenever the PID is not readily visible or located nearby. For example, an implantable PMD might be located in a different room than an RF-telemetry capable PID, even though the patient and caregiver are physically in the same room. As a further example, a patient might have an at-home PID, such as a personal communicator, that his caregiver seeks to remotely interrogate from his clinic. Although neither the caregiver's identity nor his authorization to interrogate is in question, the caregiver must still ensure that the correct PID is interrogating the receiving PMD. In both situations, the identity and authority of the PID itself are unknown to and unconfirmed by the PMD and patient safety cannot be assured.

Hybrid approaches to identification and authorization are inadequate. For example, patient consent and authorization can be obtained conventionally through wanded inductive telemetry, after which interrogation or programming can proceed using RF telemetry. However, duplicative interfaces are needed and fewer of the benefits afforded by long range interrogation are enjoyed, such as interrogation or programming performed entirely outside of a clinic or hospital.

SUMMARY

Effective identification and authorization can be achieved by establishing trust relationships between PIDs and PMDs. Both PIDs and PMDs receive a set of "master" credentials from a manufacturer certification authority or other authorizing agent prior to being put into operation or Initialization. The "master" credentials are issued by a root certification authority on behalf of the manufacturer certification authority. The PIDs also receive digitally signed permission from the manufacturer certification agent that can be presented as identification credentials to receiving PMDs for proof of identity, that is, permission to interrogate or program the PMDs. The identification credentials authenticate a particular PID to a receiving PMD to establish a basic trust relationship. "Authentication" refers to verifying the digital identity of the sender of the credentials. Thus, the PMD is assured that the PID's identity is known and that the PID is properly authorized to interrogate or program the PMD.

In a further embodiment, the identification credentials can be supplemented with access credentials, which are periodically issued by a manufacturer verification authority or other verification agent. The access credentials can be presented to receiving PMDs to establish an enhanced trust relationship. The authorization credentials can include temporal limits on when the authorization credentials are effective and restrictions on allowed operations.

One embodiment provides a system and method for confirming identity and authority by a patient medical device. Master credentials are issued to a requesting device and a receiving device from an authorizing agent. The master credentials include a public key of the authorizing agent and a digital signature of a root certification authority. Device credentials are issued to the requesting device from the authorizing agent. The device credentials include a public key of the requesting device and a digital signature of the authorizing agent. Identification credentials are provided to the receiving device and include the device credentials and a digital signature of the requesting device. The requesting device is authenticated. The digital signature of the authorizing agent in the device credentials is checked using the public key of the authorizing agent in the master credentials of the receiving device. The digital signature of the requesting device in the identification credentials is checked using the public key of the requesting device in the device credentials.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Although described in this application in relation to PMDs primarily intended for providing cardiac and cardiopulmonary therapy or monitoring, the embodiments described apply generally to all forms of PMDs capable of being remotely interrogated or programmed.

Remote Patient Management Environment

Figure 1:
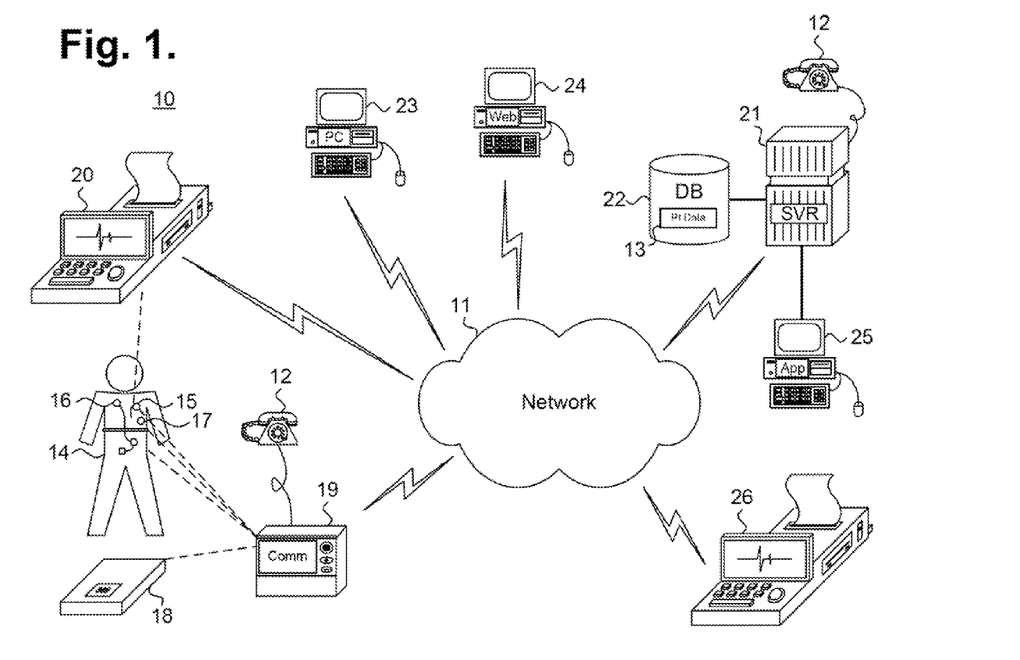
FIG. 1 is a functional block diagram showing, by way of example, a remote patient management environment.

Reliable and trustworthy identification and authorization between a PMD and a PID are most needed when the PMD and PID are physically apart, such as in a remote patient care setting, where neither the identity nor authority of a remote PID seeking to interrogate or program a PMD are known. By way of example, FIG. 1 is a functional block diagram showing a remote patient management environment 10. A patient 14 is provided with an at-home PID, such as a personal communicator 19, that can be used to interrogate or program one or more PMDs. The PMDs can include implantable medical devices 15, such as pacemakers, implantable cardiac defibrillators, drug pumps, and neuro-stimulators; external medical devices 16, such as automatic external defibrillators; implantable sensors 17, such as heart and respiratory monitors and diagnostic multi-sensor non-therapeutic devices; and external sensors 18, such as Holter monitors, weight scales, blood pressure cuffs, and the like. Other types of implantable or external PMDs for therapeutic, diagnostic, monitoring, or other medical or patient-related purposes are possible.

One or more of the PMDs 15-18 are capable of being remotely interrogated or programmed using a PID. "Remote" interrogation or programming generally refers to PMD-PID telemetric interfacing using a means other than close proximity telemetry, such as inductive telemetry. The PID can include a personal communicator 19 or a programmer 20, both of which are within long range telemetric range of the PMDs 15-18. Each PID 19, 20 includes a user interface and includes a long range interrogation interface to the PMDs 15-18, such as RF or other forms of wireless telemetry based on, for example, "strong" Bluetooth or IEEE 802.11 wireless fidelity "WiFi" and "WiMax" interfacing standards. In addition, each PID 19, 20 can include a further interrogation interface effected through direct means, such as wired connectivity; through indirect near proximity means, such as induction; or through a combination of direct and indirect means. Other forms of interrogation interfacing are possible. In a further embodiment, the PID can also include a remotely-interfaced programmer 26, which interrogates or programs the PMDs 15-18 from outside telemetric range using either a slaved locally situated personal communicator 19; an antenna point (not shown) that serves as an RF repeater to extend telemetric range, such as described in commonly-assigned U.S. patent application Ser. No. 11/593,854, filed Nov. 6, 2006, pending, the disclosure of which is incorporated by reference; or by similar remote interrogation means. A clinic or hospital that uses RF telemetry-capable programmers would have a similar configuration. Additionally, other patient interrogation and programming devices are possible.

To facilitate remote control and data retrieval, each PID 19, 20 is interconnectable to a centralized server 21 over a network 11, such as the Internet, or through a public telephone exchange 12, such as a conventional or mobile telephone network. Retrieved patient data and other information are maintained by the centralized server 21 as patient data 13 that is stored in a database 22 or similar storage device. Caregivers are able to access and analyze retrieved patient data using a Web client 24, a dedicated application 25 executing on a personal computer, or by similar means interfaced to the centralized server 21. In a further embodiment, caregivers can also remotely program PMDs using the remote Web client 24, dedicated application 25 executing on a personal computer, or by similar means, such as described in commonly-assigned U.S. patent application Ser. No. 11/651,118, filed Jan. 8, 2007, pending, the disclosure of which is incorporated by reference. Other caregiver operations are possible. The network 11 provides conventional wired, wireless, or various combinations of interconnectivity. In one embodiment, the network 11 is based on the Transmission Control Protocol/Internet Protocol (TCP/IP) protocol suite, although other protocol suites are possible. Similarly, other network topologies and arrangements are possible.

The PMDs 15-18 collect and forward patient physiometry and parametric data as either a primary or supplemental function, as well as environmental data. Patient physiometry includes quantitative or qualitative physiological measures. Parametric data reports the status and operational characteristics of the PMD itself. Finally, environmental data includes non-patient or PMD related information, such as the ambient temperature or time of day. Other types of patient data ate possible.

Prior to attempting remote interrogation or programming, a trust relationship based on confirmed identification and authorization must be established between the initiating PID 19, 20 and the receiving PMD 15-18. A PID 19, 20 is permitted to remotely interrogate or program a PMD 15-18 only after successful trust establishment. Although a trust relationship is implicit in conventional wired or near proximity interfacing, as further described below with reference to FIG. 2, a responding PMD 15-18 is generally unable to determine whether a remote requesting PID 19, 20 is known and properly authorized where the initiating PID 19, 20 is attempting to interface through a long range interface. As a result, a trust relationship must first be established through explicit identification and authorization. For long range telemetry-capable devices, explicit identification and authorization can be used to establish and maintain both basic and enhanced trust that ensure reliable and trustworthy connections, as further described below beginning with reference to FIG. 3.

In a further embodiment, subjective impressions of personal wellness, which constitute qualitative data values, can be collected for post-programming considerations. For example, answers to health questions pertaining to patient well being can be solicited from the patient 14 and collected following a change in PMD programming. To provide subjective impressions, the patient 14 can enter their subjective data into a device that incorporates a user interface, such as a telephone handset or personal computer 23, or the personal communicator 19, if so equipped.

In a further embodiment, collected patient data can be evaluated by a personal communicator 19, programmer 20, 26, or server 21 for the occurrence of one or more chronic or acute health conditions, such as described in related, commonly-owned U.S. Pat. No. 6,336,903, to Bardy, issued Jan. 8, 2002;U.S. Pat. No. 6,368,284, to Bardy, issued Apr. 9, 2002; U.S. Pat. No. 6,398,728, to Bardy, issued Jun. 4, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference.

In a still further embodiment, patient data is safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Structurally, the servers 21 are server-grade computing platforms configured as a uni-, multi- or distributed processing systems, and the Web client 24 executes Web browser or equivalent applications on a general-purpose computing platform, such as a personal desktop or notebook computer, or other Web-enabled device. The servers 21, Web client 24, and personal computer that executes a dedicated application 25 include those components conventionally found in computing devices, such as, for example, a central processing unit (CPU), memory, network interface, persistent storage, and various components for interconnecting these components.

Prior Art Implanted Medical Device Identification and Authorization

Figure 2:
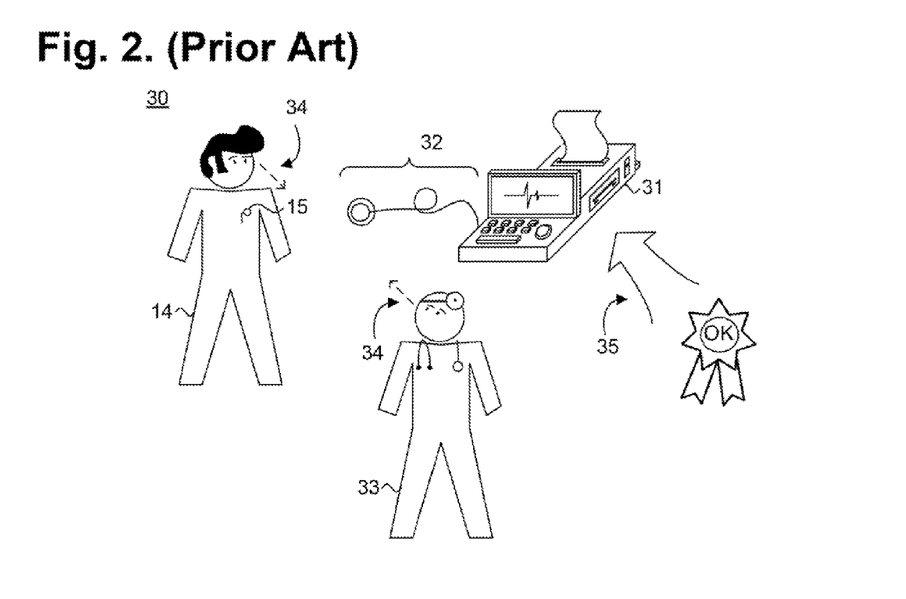
FIG. 2 is a block diagram showing, by way of example, a prior art interrogation of an implanted medical device using a conventional inductive telemetry programmer.

Identification and authorization of a requesting PID prior to commencing interrogation or programming has conventionally depended upon visual and physical proximity, as well as manufacturer quality assurances to guarantee correct PID operation and regulatory compliance. FIG. 2 is a block diagram showing, by way of example, a prior art interrogation 30 of an implanted medical device 15 using a conventional inductive telemetry programmer 31. Programming would require similar identification and authorization.

Conventionally, to interrogate the implanted medical device 15, a caregiver 33 places an inductive wand 32 over the implant location. The near physical proximity of the caregiver 33 and patient 14 enables each to visually identify the other 34, thereby ensuring that the proper patient is being interrogated by a caregiver who is proceeding with implicit patient consent. Additionally, the caregiver's physical custody of the programmer 31 provides assurances that the programmer 31 is known, unaltered, and operating in accordance with safety guidelines and certification requirements 35, which are in turn based upon the manufacturer's quality standards. Thus, the identities of the participating individuals, that is, the patient and caregiver, and of the requesting PID and receiving PMD are ail well established. The necessary permission to interrogate, that is, authorization, is also implicitly provided by the known caregivers' custody and use of a trustworthy programmer.

Confirmed Identification and Authorization Environment

A long range telemetry-capable PMD, such as an RF- or wireless-capable PMD, is generally unable to avoid communicating with an illicit or "rogue" PID, such as a stolen or improperly modified programmer, which introduces the need for a PMD to have other means to protect itself against unauthorized interrogation or programming attempts. The need can arise in any situation in which a PMD must confirm the identity and authority of a PID to interrogate or program. The situation includes an environment in which a requesting PID and receiving PMD are located at appreciable physical distance, such as a remotely-interfaced programmer communicating with a PMD through an at-home communicator, which functions as an intermediary between the programmer and PMD. The situation also includes an in-clinic environment In which a PID can interface through long range telemetry, such as RF telemetry, and therefore poses a risk of miscommunicating with the wrong PMD. Other situations are possible.

Distributed Trust Management

Safety between a requesting PID and a receiving PMD can be assured by establishing a trust relationship. The trust relationship is based upon confirmed identification and authorization, which is established through the exchange of digital credentials. Basic and enhanced trust relationships can be formed. Both types of trust relationship are established through a digital data security infrastructure, such as a public key cryptographic system, such as RSA or ECC, which uses digital asymmetric public and private key pairs. In a further embodiment, a private digital key holder can also create digitally signed messages, such as X.509 digital certificates, using their private key, which can be digitally authenticated by a recipient using the corresponding public key. Other trust relationships and digital credentials are possible.

Figure 3:
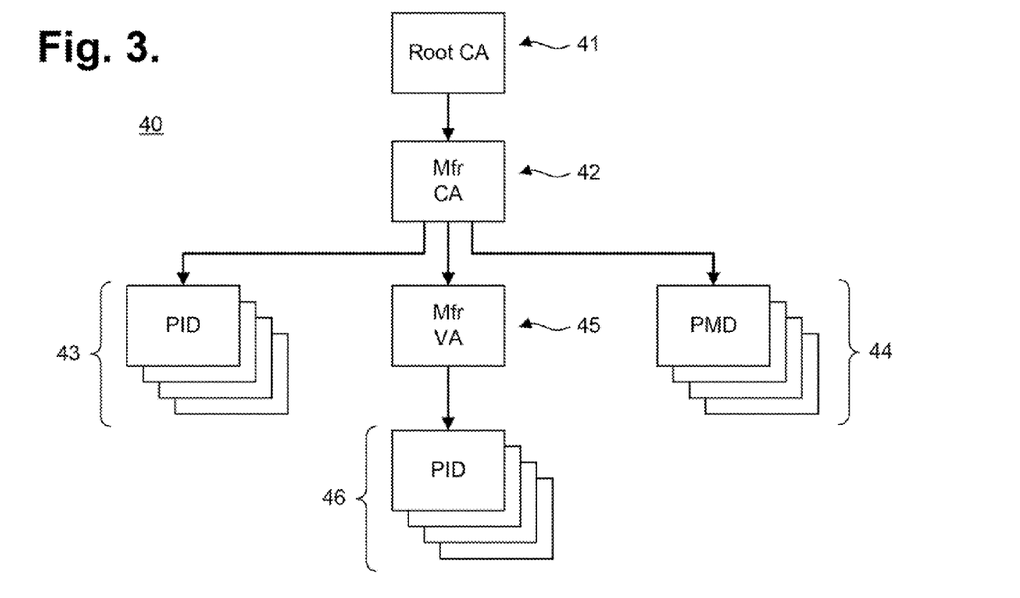
FIG. 3 is a tree diagram showing, by way of example, a hierarchy of distributed trust certifications.

To protect against loss of security through compromise or theft, trust granting authority can be delegated or distributed, such as by employing a hierarchy of authorizing agents. FIG. 3 is a tree diagram showing, by way of example, a hierarchy 40 of distributed trust certifications. Although described as a tree structured hierarchy, other structures for trust delegation are possible.

Hierarchical trust relationships depend upon a chain of authorizing agents, the most critical of which is known as a root certification authority 41. The root certification authority 41 is the most trusted of all trust relationships and is at the top of the hierarchy 40. The root certification authority 41 can delegate trust granting authority to primary certification authorities or authorizing agents, such as a manufacturer certification authority 42. In turn, the manufacturer certification authority 42 can further delegate trust granting authority to secondary certification authorities or authorizing agents, such as a manufacturer verification authority 45. Further delegations of trust granting authority are possible.

Each certification authority or authorizing agent can also issue trust credentials to individual devices. For instance, the manufacturer certification authority 42 can issue identification credentials to PIDs 43 and PMDs 44. Similarly, a manufacturer verification authority 45 can issue authorization credentials to PIDs 46, which the temporal limits by fixed time period or date and restrictions on operations permitted.

Each trust relationship is ultimately grounded under a single certification authority or authorizing agent that vouches for the identity and authorization of every member of its trust community. For instance, the trust community of a manufacturer certification authority 42 only includes those PIDs 43 that have received identification credentials from that manufacturer certification authority 42. To a limited extent, the trust credentials Issued by the certification authorities can be changed; however, the highest trust authority present in a device cannot be changed after the device is manufactured or initialized.

Basic Trust

Figure 4:
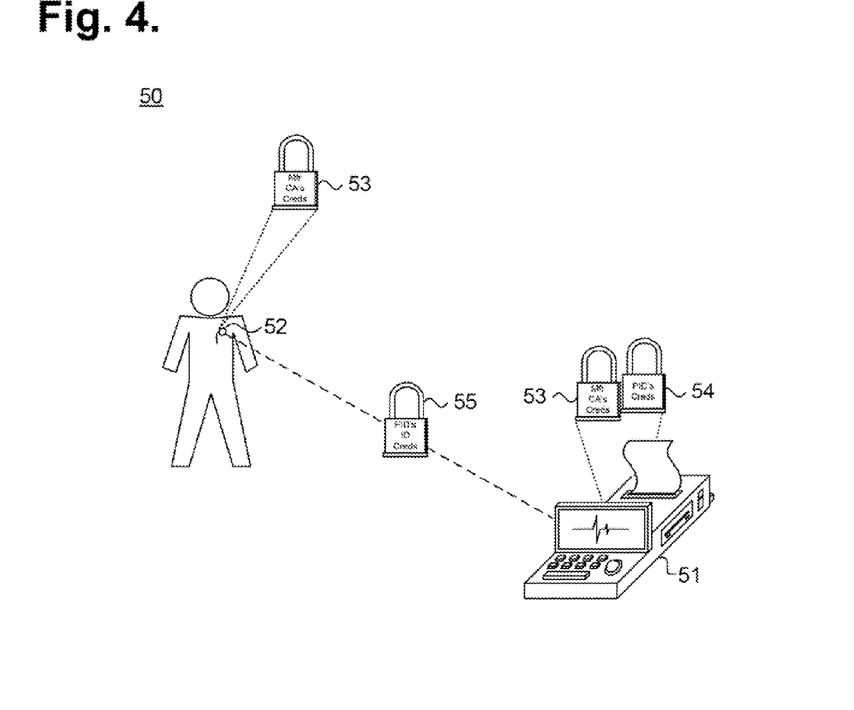
FIG. 4 is a functional block diagram showing a basic trust relationship environment, in accordance with one embodiment.

Establishing a basic trust relationship requires identification credentials, which are long terra. FIG. 4 is a functional block, diagram showing a basic trust relationship environment 50, in accordance with one embodiment. This environment 50 can be used to establish basic trust relationships in a remote patient management environment 10 (shown in FIG. 1), such as found in a clinic or hospital, or where an at-home personal communicator is used.

Prior to being put into operation or initialization, each PID 51 and PMD 52 receives manufacturer certification authority's credentials 53 from a manufacturer certification authority 42. The PID 51 also receives long-term PID's credentials 54 from the manufacturer certification authority 42. Thereafter, a basic trust relationship can be established by requiring a requesting PID 51 to prove its identity to a receiving PMD 52, either automatically or upon demand. The requesting PID 51 must present satisfactory identification credentials 55 to the receiving PMD 52 before being allowed to proceed. The identification credentials 55 are provided through secure data transfer that ensures that only the receiving PMD 52 receives the identification credentials 55. The identification credentials 55 enable the PID 51 to be recognized as belonging to a basic trust community, which signifies that the identity of the PID 51 is known and has proper authorization to interrogate or program the PMD 52.

Figure 5:
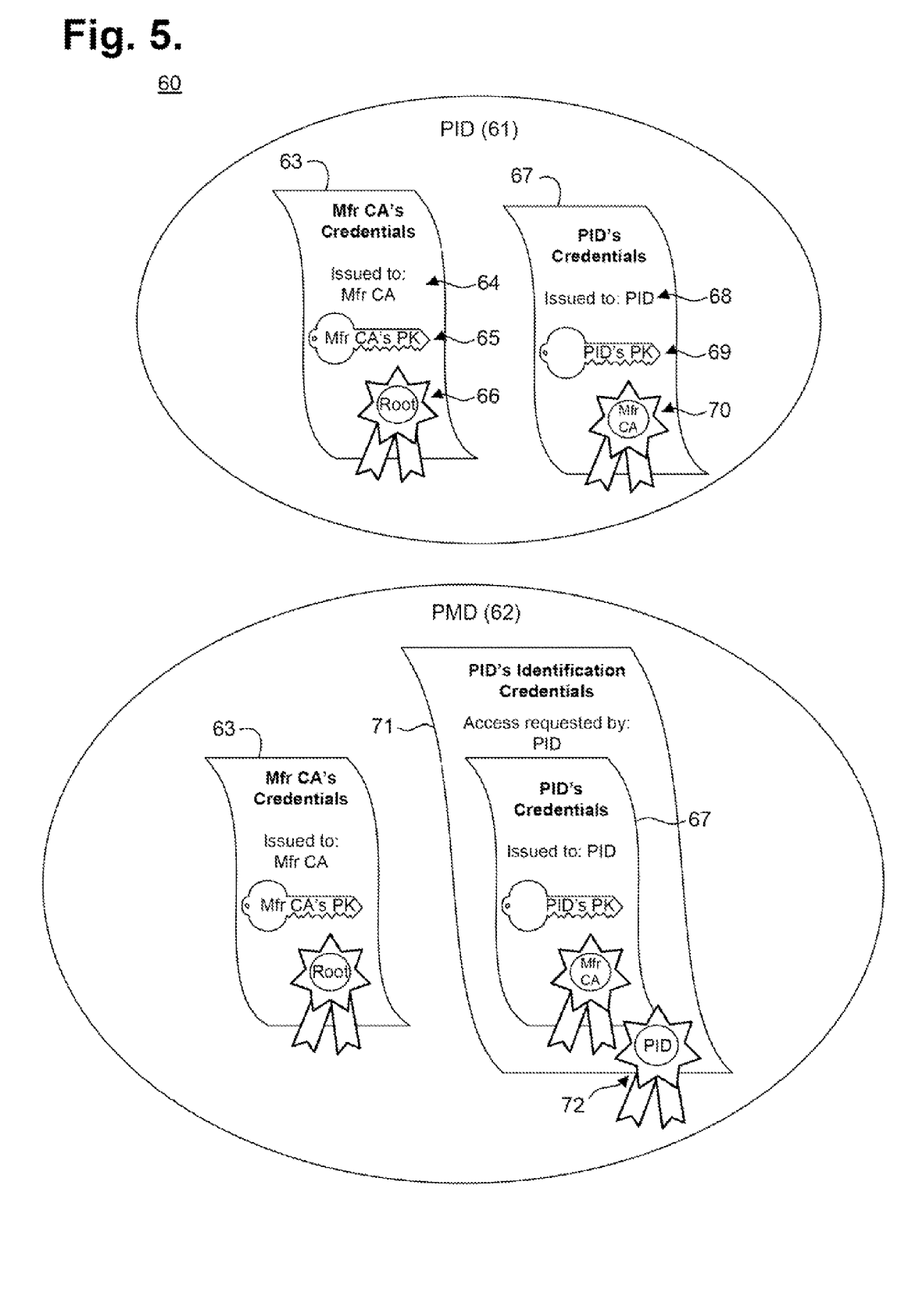
FIG. 5 is a data diagram showing credentials for a basic trust relationship for use in the environment of FIG. 4.

A basic trust relationship enables devices to recognize other members of a trust community. FIG. 5 is a data diagram showing credentials 60 for a basic trust relationship for use in the environment of FIG. 4. Each basic trust relationship relies upon credentials issued to both a PID 61 and a PMD 62. Both the PID 61 and PMD 62 receive manufacturer certification authority's credentials 63, which are issued by the root certification authority 41 to the manufacturer 64 and include the manufacturer certification authority's public key 65. The manufacturer certification authority's credentials 63 bear the root certification authority's digital signature 66. The manufacturer certification authority's credentials 63 can be used to prove membership in a trust community and are permanently maintained by the PID 61 and PMD 62, unless replaced by a new set of manufacturer certification authority's credentials 63 bearing the root certification authority's digital signature 66.

The PID 61 also receives PID's credentials 67, which are issued by the manufacturer certification authority 42 to the PID 68 and include the PID's public key 69. The PID's credentials 42 bear the manufacturer certification authority's digital signature 70. The PID's credentials 67 can also be used to prove membership in a trust community and are permanently maintained by the PID 61, unless replaced by a new set of PID's credentials 67 bearing the manufacturer certification authority's digital signature 70.

The PID 61 proves its identify to the PMD 62 by satisfactorily presenting PID's identification credentials 71. The PID's identification credentials 71 bear the PID's digital signature 72 and include a copy of the PID's credentials 67, which were issued to the PID 61 by the manufacturer certification authority 42. The PID's identification credentials 71 identify the PID 61. The PID's identification credentials 71 are authenticated by successfully checking:

(1) the manufacturer certification authority's digital signature 70 using the manufacturer certification authority's public key 65 in the manufacturer certification authority's credentials 63; and
(2) the PID's digital signature 72 using the PID's public key 69 in the PID's credentials 67.

Upon successful authentication, the PMD 62 grants permission to the PID 61 to perform interrogation or programming operations.

Enhanced Trust

A basic trust relationship may be considered sufficient for safety critical operations, such as programming, if both the receiving PMD and particularly the requesting PID are tamperproof, that is, the devices are physically secure and assured to guarantee correct operation and regulatory compliance. However, an enhanced trust relationship provides further assurances of safety by only allowing operations, such as interrogation or programming, when the requesting PID has an indication of continuing identification and authorization.

Figure 6:
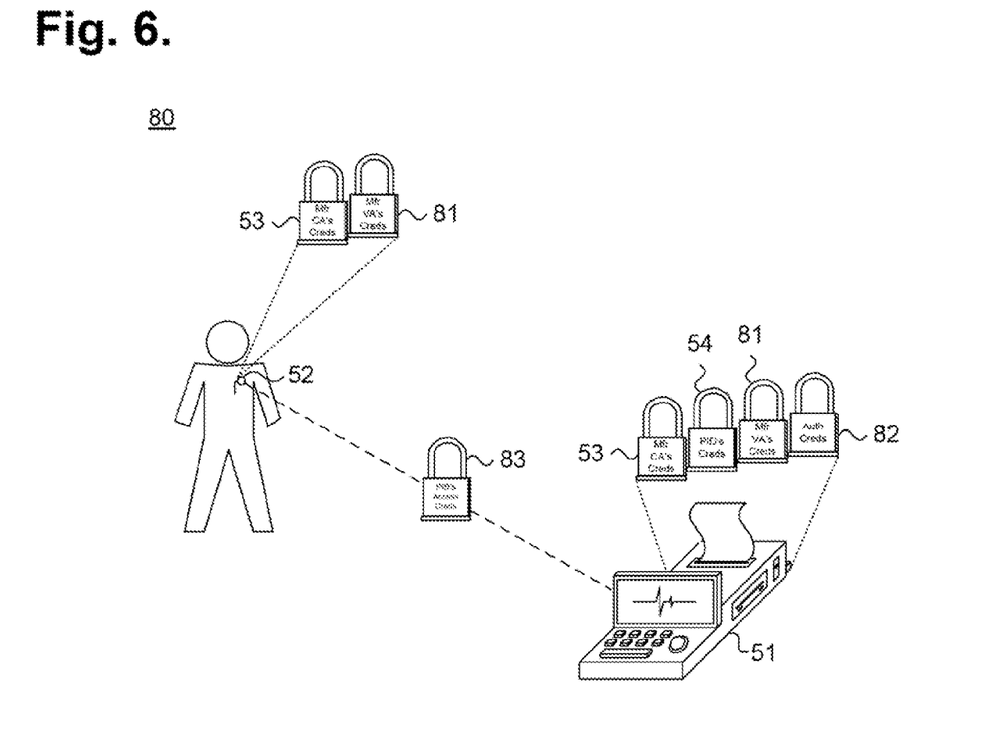
FIG. 6 is a functional block diagram showing an enhanced trust relationship environment, in accordance with a further embodiment.

A basic trust relationship can be enhanced by requiring that a requesting PID 41 be periodically re-authorized by a manufacturer verification authority 45. FIG. 6 Is a functional block diagram showing an enhanced trust relationship environment 80, in accordance with a further embodiment. This environment 80 can be used to establish enhanced trust relationships in a remote patient management environment 10 (shown in FIG. 1), such as found in a clinic or hospital, or where an at-home personal communicator is used.

As provided for basic trust relationships, each PID 51 and PMD 52 receives manufacturer certification authority's credentials 53 from a manufacturer certification authority 42 and the PID 51 also receives long-term PID's credentials 54 from the manufacturer certification authority 42. However, prior to being put into operation or initialization, each PID 51 and PMD 52 also receives manufacturer verification authority's credentials 81 from a manufacturer verification authority 42. Additionally, the PID 51 farther receives short-term authorization credentials 82 from the manufacturer verification authority 45 on a periodic, as needed, or as requested basis. Thereafter, an enhanced trust relationship can be established by requiring a requesting PID 51 to prove its identity and Its continuing permission to interrogate or program to a receiving PMD 52, either automatically or upon demand. The requesting PID 51 must present satisfactory access credentials 83 to the receiving PMD 52 before being allowed to proceed. The access credentials 83 are provided through secure data transfer that ensures that only the receiving PMD 52 receives the access credentials 83. The access credentials 83 enable the PID 51 to be recognized as belonging to an enhanced trust community, which signifies that the identity of the PID 51 is known and has proper and continuing authorization, that is, permission to interrogate or program the PMD 52.

Figure 7:
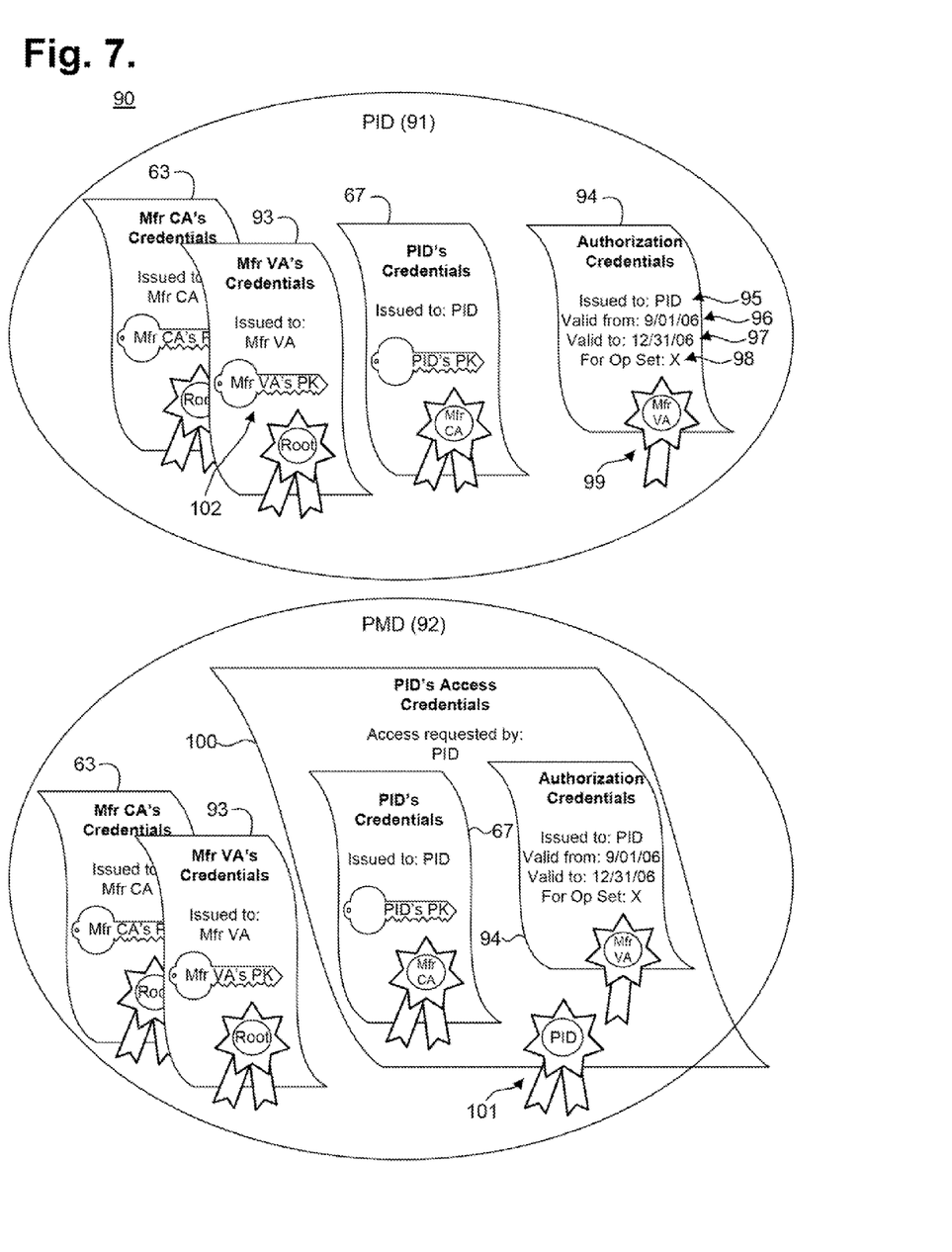
FIG. 7 is a data diagram showing credentials for an enhanced trust relationship for use in the environment of FIG. 6.

Establishing an enhanced trust relationship requires authorization credentials, which expire after a fixed time period or date. FIG. 7 is a data diagram showing credentials 90 for an enhanced trust relationship for use in the environment of FIG. 6. Each enhanced trust relationship relies upon credentials issued to both a PID 91 and a PMD 92. As for basic trust relationships, both the PID 91 and PMD 92 receive manufacturer certification authority's credentials 63 and the PID 91 also receives PID's credentials 67. Both the PID 91 and PMD 92 also receive manufacturer verification authority's credentials 93, which are issued by the roof certification authority 41 to the manufacturer 64 and Include the manufacturer verification authority's public key 102. The PID 91 also receives authorization credentials 94, which are issued by the manufacturer verification authority 45 to the PID 95 and bear the manufacturer verification authority's digital signature 99. The authorization credentials 94 can also specify permissions, limits, and restrictions on the PID 91, including dates 96, 97 during which the authorization is valid, either as a date range, expiration date; a limit on a number of sessions, including a single session limit; and a set of permitted or prohibited operations 98. Other permissions or restrictions are possible.

The authorization credentials 94 are maintained by the PID 91 until replaced by a new set of authorization credentials 94 bearing the manufacturer verification authority's digital signature 99.

The PID 91 proves its identify and its continuing permission to interrogate or program to the PMD 92 by satisfactorily presenting PID's access credentials 100. The PID's access credentials 100 bear the PID's digital signature 101 and include a copy of the PID's credentials 67 and the authorization credentials 94, which were issued to the PID 91 by the manufacturer verification authority 45. The PID's access credentials 100 identify the PID 91 and the authorization credentials 94 show continuing permission. The PID's access credentials 100 are authenticated by successfully checking:

(1) the manufacturer certification authority's digital signature 70 using the manufacturer certification authority's public key 65 in the manufacturer certification authority's credentials 63;
(2) the manufacturer verification authority's digital signature 99 using the manufacturer verification authority's public key 102 in the manufacturer verification authority's credentials 93;
(3) the PID's digital signature 101 using the PID's public key 69 in the PID's credentials 67; and
(4) the limits and restrictions on the fixed time period or date 96, 97 and set of permitted operations 98.

Upon successful authentication, the PMD 92 grants permission to the PID 91 to perform interrogation or programming operations.

While the invention has been particularly shown and described as referenced to the embodiments thereof, those skilled in the art will understand that the foregoing and other changes in form and detail may be made therein without departing from the spirit and scope of the invention.

What is claimed is:

1. A system for confirming identity and authority by a patient medical device, comprising:
    master credentials issued to a requesting device and an implantable medical device from an authorizing agent comprising a public key of the authorizing agent, a public key of a verification agent, and a digital signature of a root certification authority;
    device credentials issued to the requesting device from the authorizing agent comprising a public key of the requesting device and a digital signature of the authorizing agent;
    short-term authorization credentials issued to the requesting device from the verification agent comprising a digital signature of the verification agent, the short-term authorization credentials including an expiration date;
    access credentials provided to the implantable medical device, the access credentials comprising the device credentials, the short-term authorization credentials, and a digital signature of the requesting device; and
    an authentication module configured to authenticate the requesting device, comprising:
    a device credential module configured to check the digital signature of the authorizing agent in the device credentials using the public key of the authorizing agent in the master credentials of the implantable medical device; and
    an identification credential module configured to check the digital signature of the requesting device in the access credentials using the public key of the requesting device in the device credentials; and
    an authorization credentials module configured to check the digital signature of the verification agent in the short term authorization credentials using the public key of the verification agent in the master credentials of the implantable medical device and verify that the expiration date has not passed; and
    a reauthorization module to get updated short term authorization credentials from the verification agent with an updated expiration date.

2. A system according to claim 1, wherein one of interrogation and programming of the implantable medical device are permitted upon successful authentication of the requesting device.

3. A system according to claim 1, further comprising:
    at least one of permissions, limits, and restrictions on the requesting device included in the authorization credentials, wherein the at least one permission, limit, and restriction in the access credentials are checked.

4. A system according to claim 3, wherein the at least one permission, limit, and restriction is selected from the group comprising a limit on a number of sessions, set of permitted operations, and set of prohibited operations.

5. A system according to claim 3, wherein one of interrogation and programming of the implantable medical device within the at least one permission, limit, and restriction are permitted upon successful authentication of the requesting device.

6. A system according to claim 1, wherein the master credentials, further master credentials, device credentials, and authorization credentials comprise digital asymmetric public and private key pairs.

7. A system according to claim 1, further comprising:
    a chain of trust, comprising a root certification authority, wherein the trust is delegated to one or more further certification authorities from the root certification authority.

8. A system according to claim 7, wherein the chain of trust is structured as a hierarchy and the further certification authorities inherit the trust from the root certification authority.

9. A system according to claim 1, wherein the requesting device is selected from the group comprising a programmer and a personal communicator, each of which can interrogate or program, the implantable medical device using long range telemetry.

10. A system according to claim 1, wherein the implantable medical device comprises a device selected from the group comprising a pacemaker, implantable cardioverter-defibrillator, and cardiac synchronization therapy device.

11. A method for confirming identity and authority by a patient medical device, comprising:
    issuing master credentials to a requesting device and a implantable medical device from an authorizing agent comprising a public key of the authorizing agent, a public key of a verification agent, and a digital signature of a root certification authority;
    issuing device credentials to the requesting device from the authorizing agent comprising a public key of the requesting device and a digital signature of the authorizing agent;
    issuing short-term authorization credentials to the requesting device from the verification agent comprising a digital signature of the verification agent, the short-term authorization credentials including an expiration date;
    providing access credentials to the implantable medical device, the access credentials comprising the device credentials, the short-term authorization credentials, and a digital signature of the requesting device; and authenticating the requesting device, comprising:
checking the digital signature of the authorizing agent in the device credentials using the public key of the authorizing agent in the master credentials of the implantable medical device
checking the digital signature of the requesting device in the access credentials using the public key of the requesting device in the device credentials;
checking the digital signature of the verification agent in the short-term authorization credentials using the public key of the verification agent in the master credentials of the implantable medical device and verifying that the expiration date has not passed; and
getting updated short-term authorization credentials from the verification agent with an updated expiration date.

12. A method according to claim 11, further comprising:
permitting one of interrogation and programming of the implantable medical device upon successful authentication of the requesting device.

13. A method according to claim 11, further comprising:
including at least one of permissions, limits, and restrictions on the requesting device in the authorization credentials; and
checking the at least one permission, limit, and restriction in the access credentials.

14. A method according to claim 13, wherein the at least one permission, limit, and restriction is selected from the group comprising a limit on a number of sessions, set of permitted operations, and set of prohibited operations.

15. A method according to claim 13, further comprising:
permitting one of interrogation and programming of the implantable medical device within the at least one permission, limit, and restriction upon successful authentication of the requesting device.

16. A method according to claim 11, wherein the master credentials, further master credentials, device credentials, and authorization credentials comprise digital asymmetric public and private key pairs.

17. A method according to claim 11, further comprising:
defining a chain of trust, comprising a root certification authority; and
delegating the trust to one or more further certification authorities from the root certification authority.

18. A method according to claim 17, further comprising:
structuring the chain of trust as a hierarchy, wherein the further certification authorities inherit the trust from the root certification authority.

19. A method according to claim 11, wherein the requesting device is selected from the group comprising a programmer and a personal communicator, each of which can interrogate or program the receiving device using long range telemetry.

20. A method according to claim 11, wherein the implantable medical device comprises a device selected from the group comprising a pacemaker, implantable cardioverter-defibrillator, and cardiac resynchronization therapy device.

* * * * *